(12) United States Patent
Fossel

US008603519B2

(10) Patent No.: US 8,603,519 B2
(45) Date of Patent: *Dec. 10, 2013

(54) TOPICAL DELIVERY OF L-ARGININE TO CAUSE BENEFICIAL EFFECTS

(75) Inventor: Eric T. Fossel, Chestnut Hill, MA (US)

(73) Assignee: Strategic Science & Technologies, LLC, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/833,874

(22) Filed: Jul. 9, 2010

(65) Prior Publication Data

US 2010/0291195 A1 Nov. 18, 2010

Related U.S. Application Data

(63) Continuation of application No. 08/932,227, filed on Sep. 17, 1997, now Pat. No. 7,914,814.

(51) Int. Cl.
*A61K 9/127* (2006.01)
*A61K 31/198* (2006.01)
*A61P 15/10* (2006.01)

(52) U.S. Cl.
USPC ........... 424/450; 514/565; 514/880; 514/929; 514/946

(58) Field of Classification Search
USPC .................. 514/565, 946, 929, 880; 424/450
See application file for complete search history.

(56) References Cited

U.S. PATENT DOCUMENTS

| | | | |
|---|---|---|---|
| 3,960,782 A | 6/1976 | Daley et al. | |
| 4,185,100 A | 1/1980 | Rovee et al. | |
| 4,681,897 A | 7/1987 | Brand | |
| 4,702,913 A | 10/1987 | Marty | |
| 4,722,837 A | 2/1988 | Cameron | |
| 4,732,892 A | 3/1988 | Sarpotdar et al. | |
| 4,871,839 A | 10/1989 | Gibson | |
| 4,945,901 A * | 8/1990 | Burcke, Jr. | 601/157 |
| 4,950,654 A | 8/1990 | Horn et al. | |
| 4,976,952 A | 12/1990 | Lang et al. | |
| 5,028,435 A | 7/1991 | Katz et al. | |
| 5,158,761 A * | 10/1992 | Kamishita et al. | 424/45 |
| 5,180,743 A | 1/1993 | Watanabe et al. | |
| 5,210,099 A | 5/1993 | Mody et al. | |
| 5,215,759 A | 6/1993 | Mausner | |
| 5,217,652 A | 6/1993 | Iovanni | |
| 5,217,997 A | 6/1993 | Levere et al. | |
| 5,254,331 A | 10/1993 | Mausner | |
| 5,256,678 A | 10/1993 | Nakaguchi | |
| 5,332,758 A | 7/1994 | Nakata et al. | |
| 5,391,550 A | 2/1995 | Carniglia et al. | |
| 5,405,919 A | 4/1995 | Keefer et al. | |
| 5,428,070 A | 6/1995 | Cooke et al. | |
| 5,439,938 A | 8/1995 | Snyder et al. | |
| 5,464,954 A | 11/1995 | Kimura et al. | |
| 5,476,852 A | 12/1995 | Cauwenbergh | |
| 5,498,420 A | 3/1996 | Edgar et al. | |
| 5,505,958 A | 4/1996 | Bello et al. | |
| 5,527,797 A | 6/1996 | Eisenberg et al. | |
| 5,538,740 A | 7/1996 | Abad | |
| 5,543,430 A | 8/1996 | Kaesemeyer | |
| 5,573,776 A | 11/1996 | Harrison et al. | |
| 5,576,351 A | 11/1996 | Yoshimura et al. | |
| 5,595,753 A | 1/1997 | Hechtman | |
| 5,605,685 A | 2/1997 | Tseng et al. | |
| 5,629,002 A | 5/1997 | Weuffen et al. | |
| 5,632,981 A | 5/1997 | Saavedra et al. | |
| 5,645,859 A | 7/1997 | Chaudhuri et al. | |
| 5,648,101 A | 7/1997 | Tawashi | |
| 5,656,264 A | 8/1997 | Hanada et al. | |
| 5,691,423 A | 11/1997 | Smith et al. | |
| 5,698,738 A | 12/1997 | Garfield et al. | |

(Continued)

FOREIGN PATENT DOCUMENTS

| | | |
|---|---|---|
| CA | 2337772 C | 1/2000 |
| DE | 10128910 A1 | 12/2002 |

(Continued)

OTHER PUBLICATIONS

Argiolas, A., "Nitric Oxide is a Central Mediator of Penile Erection," *Neuropharmacology*, vol. 33, No. 11, pp. 1339-1344 (1994).
BioSpace Press Release TransDermal Ibuprofen Development Complete: NDA to Be Filed Dec. 16, 2004.
Birder, et al., "Adrenergic and capasaicin evoked nitric oxide release from urothelium and afferent nerves in urinary bladder," *American Journal of Physiology*, vol. 275, pp. F226-F229 (1998). [Abstract only].

(Continued)

*Primary Examiner* — Jeffrey Mullis
(74) *Attorney, Agent, or Firm* — Wolf, Greenfield & Sacks, P.C.

(57) ABSTRACT

A preparation is disclosed for producing enhanced blood flow in tissue thus causing beneficial effects such as promoting hair growth on scalp tissue lacking sufficient hair, restoring normal sexual function in males with erectile dysfunction. Specifically, this is a preparation which provides local delivery of the amino acid L-arginine, an important biological precursor to the main substance which is responsible for relaxation of blood vessels permitting enhancement of blood flow. In the preferred embodiments, the L-arginine is provided so that it can be topically applied to the scalp or penis. The preparation also contains an agent which aids in the transfer of L-arginine into the tissue. In the preferred embodiments this agent overcomes the resistance to transfer caused by the high charge density of L-arginine. In the preferred embodiments this means is high ionic strength created by addition of choline chloride, magnesium chloride and sodium chloride. This preparation when applied nightly to scalp tissue lacking sufficient hair for a period of time causes substantial growth of hair on the scalp. Further, when applied to the penis of a subject with erectile dysfunction causes restoration of normal sexual function.

31 Claims, No Drawings

(56) References Cited

U.S. PATENT DOCUMENTS

| | | |
|---|---|---|
| 5,714,472 A | 2/1998 | Gray et al. |
| 5,762,963 A | 6/1998 | Byas-Smith |
| 5,789,442 A | 8/1998 | Garfield et al. |
| 5,807,957 A | 9/1998 | Samour et al. |
| 5,824,658 A | 10/1998 | Falk et al. |
| 5,853,768 A | 12/1998 | Altadonna |
| 5,891,459 A | 4/1999 | Cooke et al. |
| 5,891,472 A | 4/1999 | Russell |
| 5,895,658 A | 4/1999 | Fossel |
| 5,906,822 A | 5/1999 | Samour et al. |
| 5,911,980 A | 6/1999 | Samour et al. |
| 5,922,332 A | 7/1999 | Fossel |
| 5,925,372 A | 7/1999 | Berner et al. |
| 5,939,094 A | 8/1999 | Durif et al. |
| 5,976,566 A | 11/1999 | Samour et al. |
| 6,036,977 A | 3/2000 | Drizen et al. |
| 6,103,275 A | 8/2000 | Seitz et al. |
| 6,117,872 A | 9/2000 | Maxwell et al. |
| 6,207,713 B1 | 3/2001 | Fossel |
| 6,242,229 B1 | 6/2001 | Pineau et al. |
| 6,264,979 B1* | 7/2001 | Svedman ............... 424/449 |
| 6,287,601 B1 | 9/2001 | Russell |
| 6,375,672 B1 | 4/2002 | Aksan et al. |
| 6,387,081 B1 | 5/2002 | Cooper |
| 6,444,234 B1 | 9/2002 | Kirby et al. |
| 6,448,267 B1 | 9/2002 | Anggard et al. |
| 6,451,337 B1 | 9/2002 | Smith et al. |
| 6,458,841 B2 | 10/2002 | Fossel |
| 6,511,991 B2 | 1/2003 | Hrabie et al. |
| 6,538,033 B2 | 3/2003 | Bing |
| 6,558,695 B2 | 5/2003 | Luo et al. |
| 6,562,370 B2 | 5/2003 | Luo et al. |
| 6,565,879 B1 | 5/2003 | Luo et al. |
| 6,582,724 B2 | 6/2003 | Hsu et al. |
| 6,586,000 B2 | 7/2003 | Luo et al. |
| 6,602,912 B2 | 8/2003 | Hsu et al. |
| 6,617,337 B1 | 9/2003 | Wilcox |
| 6,642,260 B2 | 11/2003 | Haj-Yehia |
| 6,646,006 B2 | 11/2003 | Cooke et al. |
| 6,716,436 B1 | 4/2004 | Sequin |
| 6,719,997 B2 | 4/2004 | Hsu et al. |
| 6,747,063 B2 | 6/2004 | Adams et al. |
| 6,787,152 B2 | 9/2004 | Kirby et al. |
| 6,835,392 B2 | 12/2004 | Hsu et al. |
| 6,858,232 B2 | 2/2005 | Verbiscar |
| 7,241,456 B2 | 7/2007 | Vromen |
| 7,267,829 B2 | 9/2007 | Kirby et al. |
| 7,442,690 B2 | 10/2008 | Prejean et al. |
| 7,629,384 B2 | 12/2009 | Fossel |
| 7,914,814 B2 | 3/2011 | Fossel |
| 2002/0015713 A1 | 2/2002 | Murdock et al. |
| 2002/0037854 A1 | 3/2002 | Breton et al. |
| 2002/0041903 A1 | 4/2002 | Fossel |
| 2002/0168325 A1 | 11/2002 | Lerner et al. |
| 2002/0168424 A1 | 11/2002 | Shahinpoor et al. |
| 2003/0018076 A1 | 1/2003 | Fossel |
| 2003/0028169 A1 | 2/2003 | Fossel |
| 2003/0044439 A1 | 3/2003 | Dobson, Jr. et al. |
| 2003/0157185 A1 | 8/2003 | Paradise |
| 2003/0203915 A1 | 10/2003 | Fang et al. |
| 2004/0082659 A1 | 4/2004 | Cooke et al. |
| 2004/0228908 A1* | 11/2004 | Liu et al. ............... 424/449 |
| 2007/0065463 A1 | 3/2007 | Aung-Din et al. |
| 2007/0072847 A1 | 3/2007 | Mueller et al. |
| 2007/0087977 A1 | 4/2007 | Robbins |
| 2007/0105763 A1 | 5/2007 | Ghosh |
| 2007/0253911 A1 | 11/2007 | Tamarkin et al. |
| 2008/0045909 A1 | 2/2008 | Fossel |
| 2008/0233183 A1 | 9/2008 | McCook et al. |
| 2008/0280984 A1 | 11/2008 | Fossel |
| 2009/0105336 A1 | 4/2009 | Fossel |
| 2009/0123528 A1 | 5/2009 | Fossel |
| 2009/0221536 A1 | 9/2009 | Fossel |
| 2009/0247635 A1 | 10/2009 | Ehrenpreis |
| 2010/0196332 A1* | 8/2010 | Wichterle et al. .......... 424/93.7 |
| 2010/0196517 A1 | 8/2010 | Fossel |
| 2010/0280122 A1 | 11/2010 | Fossel |
| 2010/0291236 A1* | 11/2010 | Sadler et al. ............... 424/649 |
| 2010/0316749 A1 | 12/2010 | Fossel |
| 2010/0317737 A1 | 12/2010 | Fossel |
| 2011/0028548 A1 | 2/2011 | Fossel |
| 2011/0182977 A1 | 7/2011 | Fossel |
| 2012/0108664 A1 | 5/2012 | Fossel |
| 2012/0148665 A1 | 6/2012 | Fossel |
| 2012/0258865 A1* | 10/2012 | Short et al. ............... 506/1 |

FOREIGN PATENT DOCUMENTS

| | | |
|---|---|---|
| EP | 0338291 A1 | 10/1989 |
| EP | 0391342 A1 | 10/1990 |
| EP | 0 399 765 A2 | 11/1990 |
| EP | 0 424 028 A2 | 4/1991 |
| EP | 1210933 A1 | 6/2002 |
| FR | 5940 | 10/1966 |
| FR | 1553063 | 11/1967 |
| FR | 2602678 | 2/1988 |
| FR | 2740453 | 4/1997 |
| FR | 2810540 | 12/2001 |
| GB | 2094142 A | 9/1982 |
| GB | 2126868 A | 4/1984 |
| JP | 57-053404 A | 3/1982 |
| JP | 03-093707 | 4/1991 |
| JP | 04005231 | 9/1992 |
| JP | 6-247832 | 9/1994 |
| JP | 6-287135 A | 10/1994 |
| JP | 7-53336 | 2/1995 |
| JP | 9-208460 A | 8/1997 |
| JP | 9-241156 A | 9/1997 |
| JP | 10-167953 | 6/1998 |
| JP | 2000-186028 A | 7/2000 |
| JP | 2001-288068 A | 10/2001 |
| JP | 2002-003373 A | 1/2002 |
| JP | 2003-286129 A | 10/2003 |
| JP | 2005-200370 A | 7/2005 |
| WO | WO 88/06034 A1 | 8/1988 |
| WO | WO 92/08705 | 5/1992 |
| WO | WO 92/15276 A2 | 9/1992 |
| WO | WO 94/09750 A1 | 5/1994 |
| WO | WO 95/13060 | 5/1995 |
| WO | WO 95/15147 | 6/1995 |
| WO | WO 96/08966 A1 | 9/1995 |
| WO | WO 96/14748 | 5/1996 |
| WO | WO 96/29988 A1 | 10/1996 |
| WO | WO 97/10830 A1 | 3/1997 |
| WO | WO 97/16983 | 5/1997 |
| WO | WO 97/39760 A1 | 10/1997 |
| WO | WO 99/13717 A1 | 3/1999 |
| WO | WO 00/03689 A2 | 1/2000 |
| WO | WO 00/40215 A1 | 7/2000 |
| WO | WO 00/54773 A1 | 9/2000 |
| WO | WO 00/69469 A1 | 11/2000 |
| WO | WO 01/45713 A1 | 6/2001 |
| WO | WO 03/049593 | 6/2003 |
| WO | WO 03/072039 | 9/2003 |
| WO | WO 03/078437 A1 | 9/2003 |
| WO | WO 03/080104 A2 | 10/2003 |
| WO | WO 2005/081964 A2 | 9/2005 |
| WO | WO 2005/102282 A2 | 11/2005 |
| WO | WO 2005/102307 A2 | 11/2005 |
| WO | WO 2006/096360 A1 | 9/2006 |

OTHER PUBLICATIONS

Bunker, C.B., et al., "Alterations in scalp blood flow after the epicutaneous application of 3% minoxidil and 0.1% hexyl nicotinate in alopecia," *Correspondence*, pp. 668-669 (1986).

Cooper, et al., "Transdermal Delivery of Drugs," *CRC Press*, vol. II, pp. 57-62 (1987).

De Boer, E.M., et al., "Does Topical Minoxidil Increase Skin Blood Flow?", *Acta Derm Venereol*, vol. 68, pp. 271-274 (1988).

Dietz, N.M., et al., "Is nitric oxide involved in cutaneous vasodilation during body heating in humans?" *J. Appl. Physiol*, vol. 76, No. 5, pp. 2047-2053 (1994).

(56) References Cited

OTHER PUBLICATIONS

Fossel, Eric T. "Improvement of Temperature and Flow in Feet of Subjects with Diabetes With Use of a Transdermal Preparation of L-Arginine" Diabetes Care, vol. 27, No. 1, Jan. 2004, pp. 284-285.
Garban, H., et al., "Effect of aging on nitric oxide-mediated penile erection in rats," Am. J. Physiol., H467-H475 (1995).
Haldiya, Kripa Ram et al. "Dermal Ulcers and Hypertension in Salt Workers" Current Science, vol. 87, No. 8, Oct. 25, 2004, pp. 1139-1141.
Hirvonen, J. et al. "Effect of diffusion potential, osmosis and ion-exchange on transdermal drug delivery: theory and experiments", Jornal of Controlled Release 56 (1998) 33-39.
Hwang, T.I., et al., "Evaluation of Vasculogenic Impotence Using Dynamic Penile Washout Test," J. Formosan Med. Assoc., vol. 89, No. 11, pp. 992-996 (1990).
Kirkeby, H.J., et al., "Role of the L-arginine/nitric oxide pathway in relaxation of isolated human penile cavernous tissue and circumflex veins," Acta Physiol Scand., vol. 149, pp. 385-392 (1993).
Klemp, P., et al., "Subcutaneous Blood Flow in Early Male Pattern Baldness," J. Invest. Dermatol., 92, pp. 725-726 (1989).
Laan, E., et al., "Assessment of female sexual arousal: Response specificity and construct validity," Psychophysiology, vol. 32, pp. 476-485 (1995).
Mathias, B. J., et al., "Topical Capsaicin for Chronic Neck Pain," Am. J. Phys. Rehabil., vol. 74, pp. 39-44 (1995).
Matuszak, Daniel et al. "Thermodynamic Driving Force for Molecular Diffusion—Lattice Density Functional Theory Predictions" J. Non-Equilib. Thermodyn. 2006 vol. 31, pp. 355-384.
Moody, J.A., et al., "Effects of Long-Term Oral Administration of L-arginine on the Rat Erectile Response," The Journal of Urology, vol. 158, pp. 942-947 (1997).
Nakaki, T. et al., "Beneficial Circulatory Effect of L-Arginine," Jpn. J. Pharmacol. 66, 167-171 (1994).
Owen, J.A., et al., "Topical Nitroglycern: A Potential Treatment for Impotence," The Journal of Urology, vol. 143, pp. 546-548 (1989).
Riedel, et al., "Different Mechanisms of L-Arginine Induced Dilation of Brain Arterioles in Normotensive and Hypertensive Rats", CA: 122 (11) 130053t [Abstract only].
Singh, S., et al., "Response of digital arteries to endothelium dependent and independent vasodilators in patients with Raynaud's phenomenon," European Journal of Clinical Investigation, vol. 25, pp. 182-185 (1995).
Sonntag, M., et al., "Role of nitric oxide in local blood flow control in the anaesthetized dog," European Journal of Physiology, pp. 194-199 (1992).
Suhonen, T. Marjukka et al. "Epidermal Cell Culture Model Derived From Rat Keratinocytes with Permeability Characteristics Comparable to Human Cadaver Skin" European Journal of Pharmaceutical Sciences 20 (2003) pp. 107-113.
The Merck Index, An Encyclopedia of Chemicals, Drugs, and Biologicals, Twelfth Edition, p. 817.
Tseng, L.F., et al., "Increase of nitric oxide production by L-arginine potentiates i.c.v. administered β-endorphin-induced antinociception in the mouse," European Journal of Pharmacology, vol. 212, pp. 301-303 (1992).
Wang, R. et al., "Nitric Oxide Mediates Penile Erection in Cats," The Journal of Urology, vol. 151, pp. 234-237 (1994).
Whitmore, E.S., et al., "Acute Effect of Topical Minoxidil on Digital Blood Flow in Patients with Raynaud's Phenomenon," The Journal of Rheumatology, vol. 22, No. 1, pp. 50-54 (1995).
International Preliminary Report on Patentability and Written Opinion of the International Searching Authority for International Application No. PCT/US2005/013228, mailed Jul. 15, 2005.
International Preliminary Report on Patentability and Written Opinion of the International Searching Authority for International Application No. PCT/US2005/013230, mailed Oct. 28, 2005.
International Preliminary Report on Patentability and Written Opinion of the International Searching Authority for International Application No. PCT/US2005/005726, mailed Sep. 8, 2006.
International Search Report for International Application No. PCT/US98/19429, mailed Jan. 11, 1999.
International Preliminary Report on Patentability and Written Opinion of the International Searching Authority for International Application No. PCT/US2009/003750, mailed May 19, 2010.
International Preliminary Report on Patentability and Written Opinion of the International Searching Authority for International Application No. PCT/US2009/003749, mailed May 19, 2010.
Thompson, P. D. "Definition and Classification of Peripheral Arterial Disease," Part IV Exercise as Adjunctive Therapy for Patients with Vascular Disease, Exercise & Sports Cardiology, 2001, p. 372.
Pauly, M. et al. "Liposomes containing amino acids and peptides and proteins for skin care," Chemical abstracts, 1998, 113:65069 (Abstract).
Flick, Cosmetics Additives: An Industrial Guide. Noyes Publications, Park Ridge, New Jersey, U.S.A. 1991: 790. (The year of publication is sufficiently earlier than the effective U.S. filing date and any foreign priority date so that the particular month of publication is not in issue. See MPEP 609.04(a)).
International Search Report and Written Opinion for PCT/US2011/067993 mailed May 1, 2012.
International Search Report and Written Opinion for PCT/US2011/067987 mailed Apr. 30, 2012.
International Search Report and Written Opinion for PCT/US2011/067991 mailed Apr. 30, 2012.
International Search Report and Written Opinion for PCT/US2011/067992 mailed Apr. 30, 2012.
International Search Report and Written Opinion for PCT/US2011/067990 mailed Apr. 30, 2012.
Extended European Search Report for EP 11182318 3 mailed Jan. 20, 2012.
Extended European Search Report for EP 11174380 3 mailed Jan. 13, 2012.
Extended European Search Report for EP 11174375 3 mailed Jan. 13, 2012.
International Preliminary Report on Patentability for PCT/US2009/003750 mailed Jan. 12, 2012.
International Preliminary Report on Patentability for PCT/US2009/003749 mailed Jan. 12, 2012.
Boger et al., Restoring vascular nitric oxide formation by L-arginine improves the symptoms of intermittent claudication in patients with peripheral arterial occlusive disease. J Am Coll Cardiol. Nov. 1998;32(5):1336-44.
Extended Europrean Search Report for EP 09014985 7 mailed Apr. 22, 2010.
Extended European Search Report for EP 11173316 8 mailed Sep. 22, 2011.
International Preliminary Examination Report for PCT/US98/19429 mailed Apr. 6, 2000.
International Search Report and Written Opinion for PCT/US05/05726 mailed Sep. 19, 2005.
International Search Report and Written Opinion for PCT/US05/13228 mailed Jul. 15, 2005.
International Search Report and Written Opinion for PCT/US05/13230 mailed Oct. 28, 2005.
Supplementary European Search Report for EP 05723558.2 mailed Feb. 17, 2009.
Supplementary European Search Report for EP 05737752.5 mailed Apr. 21, 2009.
Supplementary European Search Report for EP 05737763.2 mailed May 12, 2009.
Supplementary European Search Report for EP 98946099.3 mailed Mar. 1, 2006.
Writtion Opinion for PCT/US98/19429 mailed Jul. 14, 1999.
[No Author Listed] "Xanthan gum used in cosmetic products." Dermaxime: bio-cellular skin products. Available at http://www.dermaxime.com/xanthan.htm. Last accessed Apr. 23, 2009. 4 pages.
[No Author Listed] Peripheral Vascular Disease (web page) http://www.americanheart.org/presenter.jhtml?identifier=4692 [Jan. 18, 2010]. 2 pages.
[No Author Listed] Peripheral Vascular Disease—Wikipedia (web page) http://en.wikipedia.org/wiki/Peripheral_vascular_disease [Jan. 18, 2010]. 5 pages.

(56) References Cited

OTHER PUBLICATIONS

Hirsch et al., Peripheral Arterial Disease Detection, Awareness, and Treatment in Primary Care. J Am Med Assoc. 2001;286(11):1317-1324.

McLatchie et al., The effects of pH on the interaction between capsaicin and the vanilloid receptor in rat dorsal root ganglia neurons. Br J Pharmacol. Feb. 2001;132(4):899-908.

Schölermann et al., Clinical and biophysical efficacy of a novel coenzyme Q10 containing anit-wrinkle cream (Eucerin® Q10 active). J Euro Acad Dermatol Venereol. 1998;11:5270. Abstract p. 364.

Shukla et al., Nitric oxide inhibits wounds collagen synthesis. Mol Cell Biochem. Oct. 1999; 200(1-2):27-33.

Japanese Office Action for Application No. 2011-93358 mailed Nov. 1, 2012.

[No Author Listed] MoonDragon's Health & Wellness: Nutrition Basics: Amino Acids-Arginine. Last Accessed on Aug. 28, 2012 from http://www.moondragon.org/health/nutritionbasics/aminoacids/arginine.html. 10 pages.

[No Author Listed] "Xanthan gum." Wikipedia. Last Accessed on Apr. 13, 2009 from http://en.wikipedia.org/wiki/Xanthan. 3 pages.

[No Author Listed] Sex and Sexuality Orgasm Information. Extended Orgasm (web page). May 2000. 7 pages.

Bessatsu, Igaku no Ayumi, Shinkei Shikkan (A Separate Volume: Progress in Medicine, Neurological Desiases), 1999:314-6. Chinese.

Biagini et al., [Intermittent claudication: topical treatment with isosorbide dinitrate ointment. Preliminary results]. G Ital Cardiol. 1981;11(7):514-521.

Goldenberg, The Care of the Diabetic Foot. Judy Dan Research & Treatment Centre. Last Accessed on Sep. 20, 2010 from http://www.ontariowoundcare.com/footcarephysician.htm. 9 pages.

Gutman et al., Molecular discovery of transdermal delivery nanotechnology from computer experiments and experimental R & D. Strategic Science Technologies. Presented at the Langer USA-Japan Drug Delivery Conference. Maui, Hawaii. Dec. 2011. 21 pgs.

Rinshyo, Treatment and prevention of diabetic foot ulcer. Shin Jidai no Tonyobyogaku (Studies on Diabetes in a New Age). 2002;4:354-8. Chinese.

Tiso et al., Oral versus topical ibuprofen for chronic knee pain: A prospective randomized pilot study. Pain Physician. Sep./Oct. 2010;13:457-467.

\* cited by examiner

TOPICAL DELIVERY OF L-ARGININE TO CAUSE BENEFICIAL EFFECTS

RELATED APPLICATIONS

This application is a continuation of U.S. patent application Ser. No. 08/932,227, filed Sep. 17, 1997 now U.S. Pat. No. 7,914,814, entitled "Topical Delivery of L-Arginine to Cause Beneficial Effects," by E. T. Fossel, incorporated herein by reference.

BACKGROUND

1. Field of the Invention

This invention relates to topical application of a cream, gel, or other vehicle which contains substances such as L-arginine which delivers these substances into tissue for the purpose of producing beneficial effects such as growth of hair on the scalp, healing of leg ulcers secondary to diabetes or confinement to bed and overcoming erectile dysfunction, as well as beneficial effects through restoration of natural mechanisms based on improvement of local blood supply.

2. Prior Art

Approaches to improving local blood flow have been many and consist of both systemic and topical approaches. Many beneficial effects could be obtained should improvement in local blood flow be achieved since impairment of local blood flow causes a variety of negative consequences.

It has been recognized that deficiencies in blood flow in the scalp occur in male pattern baldness. See G. Duplechain et al., *J. Louisiana State Med Soc.* 146, 7 (1994); P Klemp et al., *J Invests Dermatol* 95, 725 (1989); S Toshitani et al., *J Dermatol* 17, 240 (1990). Topical minoxidil has been used as an agent for hair growth in male pattern baldness with varying results. Though the suggestion has been made that minoxidil operates through increase in the blood supply to the scalp, many investigators have failed to show such an effect. See E de Boer et al., *Acta Dermato-Venereoligica* 68, 271 (1988); C Bunker et al., *British J Derm* 117, 668 (1987).

It has long been recognized that impaired blood flow to the penis is a major cause of erectile failure (impotence) in men. See A Moradian et al. *Am J. Med* 85, 748, (1988); T Hwang et al. *J Formosan Med Assoc* 89, 992 (1990). Further it has been recognized by using isolated tissue in vitro and in animal experiments that nitric oxide is an important mediator of relaxation of the vessels in penile cavernous tissue. See H Kirkeby et al. *Acta Physiol Scand* 149, 385 (1993). Topical nitroglycerine has been used in the treatment of impotence because of its ability to dilate vessels. The results were inconclusive and the treatment not well tolerated because of the cardiac response to nitroglycerine. See S Negelev *J Urology* 143, 586 (1990).

Accordingly, several objects and advantages of the instant invention are to induce the growth of hair on portions of human scalp which has insufficient hair by means of enhancement of the body's natural mechanisms. It is yet another object of the instant invention to induce healing of superficial ulcers of the limbs by means of enhancement of the body's natural mechanisms. It is still another object of the instant invention to overcome erectile failure restoring natural male sexual function by means of enhancement of the body's own natural mechanisms.

SUMMARY OF THE INVENTION

It was discovered that topical application of a nitric oxide precursor, L-arginine, in its various forms contained in a variety of topical preparations, either by themselves or with other agents to aid in penetration, such as a high ionic strength environment, neutralization of its charge in a complex or by other means, or included in a liposome or other biological carrier, when administered to the scalp causes hair growth, when administered to superficial ulcers causes healing and when administered to the penis enhances erectile function.

In one embodiment of the invention, a penetrating cream containing L-arginine at an effective concentration and a salt, such as sodium chloride, at a concentration sufficient to create a hostile biophysical environment for the L-arginine in the cream is applied to nightly to the scalp containing a deficit of hair induces hair growth within 3-4 months.

Further, in accordance with this invention, a penetrating cream containing L-arginine in a concentration sufficient to produce the desired effect along with sodium chloride or other salts at a concentration sufficient to produce a hostile biophysical environment when applied to the penis induces firm and natural erections within 20 minutes.

Consequently, with the discovery of the present invention, a means to restore hair growth on a portion of scalp scarce in hair has been found. Further, with the discovery of the present invention, a means to heal superficial ulcers has been found. Additionally, with the discovery of the present invention, a means to overcome erectile dysfunction has been found.

In preferred embodiments, the delivery vehicle is a penetrating cream, the L-arginine is present as L-arginine hydrochloride in a concentration sufficient to produce the desired effect and the agent which creates the hostile biophysical environment is sodium chloride at a concentration sufficient to aid in tissue absorption.

These and other objects and features of the present invention will become apparent to those skilled in the art from reading the description of the invention, which follows.

DETAILED DESCRIPTION OF THE INVENTION

The preferred embodiment consists of a base cream with the properties of excellent absorption into the skin which also contains L-arginine hydrochloride (12.5% w/v), choline chloride (10%), sodium chloride (5% w/v) and magnesium chloride (5% w/v). The components of the base cream may be those commonly found in hand creams, such as water, mineral oil, glyceryl stereate, squalene, propylene glycol stearate, wheat germ oil, glyceryl stearate, isopropyl myristate, steryl stearate, polysorbate 60, propylene glycol, oleic acid, tocopherol acetate, collagen, sorbitan stearate, vitamin A & D, triethanolamine, methylparaben, aloe vera extract, imidazolidinyl urea, propylparaben, and BHA. L-arginine hydrochloride provides a precursor to the molecule, nitric oxide, NO. Nitric oxide is the substance that relaxes the blood vessels, allowing for increased blood flow. Choline chloride, sodium chloride and magnesium chloride provides a high ionic strength environment for the highly charged molecule, L-arginine. This high ionic strength environment is an example of a hostile biophysical environment for L-arginine. That is, the highly charged ionic strength is an unfavorable environment for the highly charged L-arginine making the L-arginine anxious to move to a more hospitable, less charged environment such as human tissue. The base cream containing L-arginine, choline chloride, sodium chloride and magnesium chloride is the agent which produces beneficial effects such as hair growth, healing of ulcers such as leg ulcers or restoration of normal erectile function in males suffering from erectile dysfunction.

The cream acts effectively to induce hair growth on human scalp lacking sufficient hair when applied nightly to the bald area each night for several months. Hair growth is naturally a slow process. However, substantial hair growth is achieved over large areas of scalp with results becoming evident in a few weeks and substantial within several months. Yet further, the cream acts to promote healing of superficial ulcers such as those sometimes found on the legs of persons with severe diabetes. Application twice daily for a period of two weeks causes substantial healing and in many cases complete healing is achieved within this time period or slightly longer (3-4 weeks). Still further, the cream acts to overcome erectile dysfunction in males causing restoration of natural sexual function. These applications and others share as a common mechanism of action, improvement in local blood flow.

OTHER EMBODIMENTS

Other Active Agents

While L-arginine hydrochloride is the preferred active agent because it is the agent in nature itself, it is non-toxic, is highly soluble and it is inexpensive, other agents could be used which are also precursors or donors of nitric oxide. These include D,L-arginine, L-arginine, alkyl (ethyl, methyl, propyl, isopropyl, butyl, isobutyl, t-butyl) esters of L-arginine and salts thereof. Pharmaceutically acceptable salts include hydrochloride, glutamate, butyrate, and glycolate.

In the case of an alternative active agent were used it would be simply substituted for L-arginine in a delivery preparation and the preparation used as in the case of the L-arginine preparation.

Other Means of Effecting or Improving Absorption

A variety of means for effecting or improving absorption of the active agent can be envisioned. One principle behind the absorption of a highly charged molecule such as L-arginine into tissue is to either create a biophysically hostile environment in the delivery vehicle such that L-arginine would prefer to be in tissue, or to package L-arginine in such a way that it is carried into tissue or neutralize its charge by derivitization or forming a neutral salt. Examples of biophysically hostile environments, include but are not limited to; high ionic strength by the addition of ionic salts such as sodium chloride, magnesium chloride or choline chloride; high or low pH by adding pharmaceutically acceptable acids or bases; and highly hydrophobic environments by decreasing water content and increasing lipid, oil and/or wax content. Examples of packaging which would be carried into tissue includes liposomes or emulsions of collagen, collagen peptides or other components of skin or basement membrane. Examples of neutralization of charge include delivery of the active agent in the form or an ester or salt such as arginine glutamate which is electronically neutral.

In each case of creating a hostile biophysical environment for the active agent, the agent was added to an appropriate preparation. In the case of creating a high ionic strength ions such as but not limited to sodium chloride, potassium chloride, choline chloride, magnesium chloride, lithium chloride, alone or in combination were added in high concentration. Other highly charged molecules such as polylysine, polyglutamine, polyaspartate or copolymers of such charged amino acids may be used to create the hostile biophysical environment. Alternatively a hostile biophysical environment may be created by placing the highly charged L-arginine in an hydrophobic, oily environment such as in an oil-based cream containing little or no water. Absorption may further be aided by combining the use of hostile biophysical environments with the use of penetrating agents such as oleoresin capsicum or its constituents or molecules containing heterocyclic rings to which are attached hydrocarbon chains.

Example 1

In this example a 53 year old man with a scalp lacking sufficient hair consisting of a severely receding hairline as well as large "bald spot" on the top rear of his head was provided with a penetrating cream containing L-arginine hydrochloride (12.5% w/v), choline chloride (10% w/v), sodium chloride (5% w/v) and magnesium chloride (5% w/v). The cream was applied to the bald areas each night before going to bed and was rubbed in extensively for maximal absorption. New hair growth was noted within 2-3 weeks. Within 4 months the receding hairline (previously 4 cm of bald skin) had returned to normal and the "bald spot" previously more than 7 cm in diameter had been reduced to an area of less than 2 cm with even this area showing some new hair growth.

Example 2

In a 54 year old man with a history of impotence twice daily administration of a penetrating cream containing L-arginine hydrochloride (12.5% w/v), choline chloride (10% w/v), sodium chloride (10% w/v) and magnesium chloride (5% w/v) directly to the penis twice daily for 7 days brought initial relief from the symptoms of impotence and allowed the subject to resume normal sexual activity. This relief of symptoms was maintained by continuation of the treatment daily.

Example 3

In a 62 year old man with a history of impotence placed a condom containing a water based penetrating cream containing L-arginine hydrochloride (12.5% w/v), choline chloride (10% w/v), sodium chloride (5% w/v) and magnesium chloride (5% w/v) was warn on the flaccid penis for 30-60 minutes before erection was desired. At that time, when sexual performance was needed, an erection was easily obtained and normal sexual activity was conducted.

Accordingly, it can be seen that in the present invention I have provided agents, which when applied to scalp lacking sufficient hair causes hair growth through utilization of one of the body's own mechanisms. This effect is achieved by providing the biochemical substrate at the local site from which nitric oxide is produced. Nitric oxide causes increased local blood flow, which enables the growth of hair. Further I have provided agents which when applied to leg ulcers cause healing through use of the body's own mechanisms. Still further I have provided agents that when applied to a penis subject to erectile dysfunction causes restoration of normal sexual function. This effect is achieved by providing the biochemical substrate at the local site from which the controlling substance, nitric oxide is produced. Nitric oxide causes increases in local blood flow allowing the body's own healing cells and substances to reach the ulcer site.

Although the description above contains many specificities, these should not be construed as limiting the scope of the invention but as merely providing illustrations of some of the presently preferred embodiments of this invention. Various other embodiments and ramifications are possible within this scope.

Thus the scope of the invention should be determined by the appended claims and their legal equivalents, rather than by the examples given.

What is claimed is:

1. A composition for topical application to the skin of a subject, the composition comprising:
   a cream containing oil and water, the cream further comprising an amino acid compound consisting essentially of an L-arginine compound selected from the group consisting of L-arginine and an L-arginine salt,
   wherein the cream further comprises an ionic salt selected from the group consisting of choline chloride, magnesium chloride, and sodium chloride, wherein the ionic salt is present in the cream at a concentration (w/v) that is higher than the concentration of ionic salts in human skin.

2. The composition of claim 1, wherein the ionic salt comprises sodium chloride.

3. The composition of claim 1, wherein the ionic salt comprises magnesium chloride.

4. The composition of claim 1, wherein the ionic salt comprises choline chloride.

5. The composition of claim 1, wherein the L-arginine compound is L-arginine.

6. The composition of claim 1, wherein the L-arginine compound is L-arginine hydrochloride.

7. The composition of claim 1, wherein the L-arginine compound is contained within a liposome contained within the cream.

8. An article for topical application to the skin, the article comprising:
   a trans-dermal patch comprising an L-arginine compound selected from the group consisting of L-arginine and an L-arginine salt,
   wherein the L-arginine compound is contained within an environment comprising an ionic salt selected from the group consisting of choline chloride, magnesium chloride, and sodium chloride, wherein the ionic salt is present in the environment at a concentration (w/v) that is higher than the concentration of ionic salts in human skin.

9. A topical treatment method, comprising:
   applying a trans-dermal patch to the skin,
   wherein the trans-dermal patch comprises an L-arginine compound selected from the group consisting of L-arginine and an L-arginine salt, and
   wherein the L-arginine compound is contained within an environment comprising an ionic salt selected from the group consisting of choline chloride, magnesium chloride, and sodium chloride, wherein the ionic salt is present in the environment at a concentration (w/v) that is higher than the concentration of ionic salts in human skin.

10. The method of claim 9, wherein the L-arginine compound is packaged in such a way that the L-arginine compound is in an environment that causes the L-arginine compound to migrate from the patch into the skin once the patch is applied to the skin.

11. The method of claim 9, wherein the L-arginine compound is L-arginine.

12. The method of claim 9, wherein the L-arginine compound is L-arginine hydrochloride.

13. A method of treating a subject, comprising:
   applying a topical cream to a region on the skin of a subject where increased blood flow is desired, wherein the cream contains oil and water, the cream further comprising an L-arginine compound selected from the group consisting of L-arginine and an L-arginine salt, and wherein the cream further comprises an ionic salt selected from the group consisting of choline chloride, magnesium chloride, and sodium chloride, wherein the ionic salt is present in the cream at a concentration (w/v) of an ionic salt that is higher than the concentration of ionic salts in human skin.

14. The method of claim 13, wherein upon application of the topical cream to the region of the skin, the L-arginine compound is locally delivered to the region of skin where the topical cream is applied.

15. The method of claim 13, wherein the L-arginine compound is L-arginine.

16. The method of claim 13, wherein the L-arginine compound is L-arginine hydrochloride.

17. A method of treating a subject, comprising:
   applying a topical cream to the skin of a subject twice daily, wherein the cream contains oil and water, the cream further comprising an L-arginine compound selected from the group consisting of L-arginine and an L-arginine salt, and wherein the cream further comprises an ionic salt selected from the group consisting of choline chloride, magnesium chloride, and sodium chloride, wherein the ionic salt is present in the cream at a concentration of an ionic salt that is higher than the concentration (w/v) of ionic salts in human skin.

18. The method of claim 17, wherein the L-arginine compound is L-arginine.

19. The method of claim 17, wherein the L-arginine compound is L-arginine hydrochloride.

20. A method of increasing localized bloodflow in tissue by delivering to skin L-arginine, the method comprising the step of:
   applying topically to the skin a cream for the L-arginine, said cream containing oil and water, the cream further comprising an amount of the L-arginine effective to increase localized tissue bloodflow when combined with an agent for creating a hostile biophysical environment comprising an ionic salt mixture, the agent being at a concentration sufficient to create the hostile biophysical environment, the hostile biophysical environment causing the L-arginine to migrate from the delivery vehicle to the skin where the L-arginine is absorbed by tissue in the area surrounding the skin where the L-arginine is applied, and wherein the concentration (w/v) that is higher than the concentration of ionic salts in human skin.

21. The method of claim 20, wherein the ionic salt mixture comprises choline chloride, sodium chloride, and magnesium chloride.

22. A method, comprising:
   applying topically to the skin a cream containing oil and water, the cream further comprising L-arginine, the cream further comprising one or more ionic salts, the one or more ionic salts together having a concentration (w/v) that is higher than the concentration of ionic salts in human skin.

23. The method of claim 22, wherein the one or more ionic salts comprise sodium chloride.

24. The method of claim 22, wherein the L-arginine is present in an amount of 0.25% to 25% by weight of the cream.

25. The composition of claim 1, wherein the cream comprises glyceryl stereate.

26. The composition of claim 1, wherein the cream comprises squalene.

27. The composition of claim 1, wherein the cream comprises isopropyl myristate.

28. The composition of claim 1, wherein the cream comprises oleic acid.

29. The composition of claim 1, wherein the cream comprises propylene glycol.

30. The method of claim 13, wherein the ionic salt comprises sodium chloride.

31. The method of claim 20, wherein the ionic salt mixture comprises sodium chloride.

* * * * *